United States Patent [19]

Sugimoto et al.

[11] Patent Number: 5,306,720

[45] Date of Patent: Apr. 26, 1994

[54] PIPERIDINE DERIVATIVE AND PHARMACEUTICAL COMPOSITION

[75] Inventors: Hachiro Sugimoto, Ushiku; Takaharu Nakamura, Abiko; Yutaka Tsuchiya, Ushiku; Hiroyuki Sugumi, Yatabemachi; Kunizou Higurashi, Tokyo; Norio Karibe, Yatabemachi; Yoshiharu Yamanishi, Ryugasaki; Hiroo Ogura, Tsuchiura; Shin Araki; Atsuhiko Kubota, both of Niihari; Michiko Ohtake, Mitsukaido; Kiyomi Tamatsu, Kamakura, all of Japan

[73] Assignee: Eisai Co., Ltd., Tokyo, Japan

[21] Appl. No.: 811,698

[22] Filed: Dec. 20, 1991

Related U.S. Application Data

[62] Division of Ser. No. 679,769, Apr. 3, 1991, Pat. No. 5,118,684, which is a division of Ser. No. 479,948, Feb. 14, 1990, Pat. No. 5,039,681. which is a division of Ser. No. 321,624, Mar. 10, 1989, Pat. No. 4,942,169, which is a division of Ser. No. 946,459, Dec. 24, 1986, Pat. No. 4,849,431.

[30] Foreign Application Priority Data

Dec. 27, 1985 [JP] Japan .................... 60-293885

[51] Int. Cl.$^5$ .................. A61K 31/505; C07D 401/12
[52] U.S. Cl. .................... 514/259; 544/285; 544/350; 544/406; 546/79; 546/99; 546/113; 546/142; 546/169; 546/187; 546/194; 546/197; 546/198; 546/201; 546/206; 546/232; 546/234
[58] Field of Search .......... 544/285; 514/259

[56] References Cited

U.S. PATENT DOCUMENTS 4,335,127 6/1982 Vanderbeck et al. .......... 544/285

Primary Examiner—C. Warren Ivy
Assistant Examiner—James H. Turnipseed
Attorney, Agent, or Firm—Flynn, Thiel, Boutell & Tanis

[57] ABSTRACT

A novel piperidine derivative is defined by the formula (I), including a salt thereof,

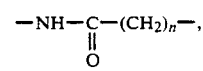

wherein
$R^1$ denotes a univalent group derived from substituted or unsubstituted quinazolinedione,
X denotes a group of the formula

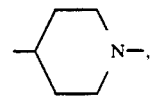

n is an integer of 1 through 7,
the ring A denotes a group of the formula

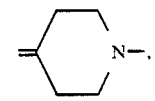

a group of the formula

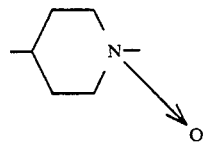

or a group of the formula

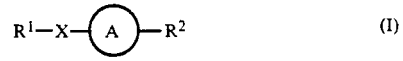

and
$R^2$ denotes a hydrogen atom, a lower alkyl group, a substituted benzoyl group, a pyridyl group, a 2-

(Abstract continued on next page.)

hydroxyethyl group, a pyridylmethyl group, or a
group of the formula
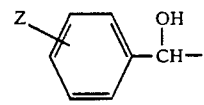
wherein Z represents a halogen atom). The novel compounds of this invention are used for treating dementias and sequelae of cerebrovascular diseases.
9 Claims, No Drawings

PIPERIDINE DERIVATIVE AND PHARMACEUTICAL COMPOSITION

This is a division of Ser. No. 07/679 769, filed Apr. 3, 1991, now U.S. Pat. No. 5,118,684 which is a division of Ser. No. 07/479 948, now U.S. Pat. No. 5,039,681 filed Feb. 14, 1990, which is a division of Ser. No. 07/321 624, filed Mar. 10, 1989, now U.S. Pat. No. 4,942,169, issued Jul. 17, 1990, which is a division of Ser. No. 06/946 459, filed Dec. 24, 1986, now U.S. Pat. No. 4,849,431, issued Jul. 18, 1989.

The present invention relates to piperidine derivatives having excellent actions as medicines. The invention relates more particularly to piperidine derivatives of the following general formula (I) or pharmacologically allowable salts thereof:

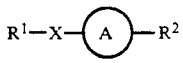

(I)

wherein $R^1$ denotes a univalent group derived from one selected among substituted or unsubstituted benzene, pyridine, pyrazine, indole, anthraquinone, quinoline, substituted or unsubstituted phthalimide, homophthalimide, pyridinecarboxylic acid imide, pyridine N-oxide, pyrazinedicarboxylic acid imide, naphthalenedicarboxylic acid imide, substituted or unsubstituted quinazolinedione, 1,8-naphthalimide, bicyclo [2.2.2] octo-5-ene-2,3-dicarboxylic acid imide and pyromerylimide, X denotes a group of the formula $-(CH_2)_n-$, a group of the formula $-O(CH_2)_n-$, a group of the formula $-S(CH_2)_n-$, a group of the formula $-NH(CH_2)_n-$, a group of the formula $-SO_2NH(CH_2)_n-$, a group of the formula

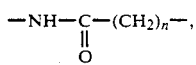

a group of the formula

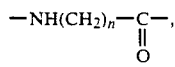

a group of the formula

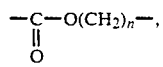

a group of the formula $-CH_2NH(CH_2)_n-$, a group of the formula

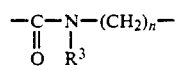

(in all the above formulas, n is an integer of 1 through 7 and $R^3$ represents hydrogen a lower alkyl group or a benzyl group), a group of the formula

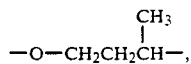

a group of the formula

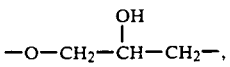

a group of the formula $-O-CH_2CH_2CH=$ or a group of the formula $$-O-CH_2-\overset{OH}{\underset{|}{CH}}-CH_2-,$$

the ring A denotes a group of the formula

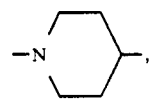

a group of the formula

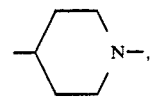

a group of the formula

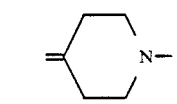

or a group of the formula

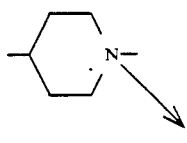

and $R^2$ denotes a hydrogen atom, a lower alkyl group, a substituted or unsubstituted benzyl group, a substituted or unsubstituted benzoyl group, a pyridyl group, a 2-hydroxyethyl group, a pyridylmethyl group or a group of the formula

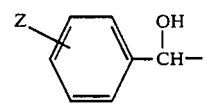

(wherein Z represents a halogen atom).

The lower alkyl group in the definition of the formula (I) means a straight-chain or branched alkyl group having 1 to 6 carbon atoms, such as methyl, ethyl, n-propyl, isopropyl, n-butyl, isobutyl, 1-methylpropyl, tert-butyl, n-pentyl, 1-ethylpropyl, isoamyl or n-hexyl. Preferable lower alkyl groups include a methyl group, ethyl group, etc. The lower alkoxy group means a group derived from the above lower alkyl group.

The univalent group derived from substituted or unsubstituted benzene in the definition of $R^1$ means specifically the following:

(1) Univalent group of the formula $$(D)_n \text{—} \bigcirc \text{—}$$

wherein n is an integer of 1 through 3 and D denotes a substituent group or two or three same or different substituent groups selected from the group consisting of a hydrogen atom, a lower alkyl group, a nitro group, a lower alkoxy group, an alkylenedioxy group formed between adjacent carbon atoms in arbitrary positions, a cyano group, a halogen atom, an amino group, a monoalkylamino or dialkylamino group, a lower alkoxycarbonyl group, a trifluoromethyl group, a formyl group, a hydroxy group (hydroxyl group), a lower alkylthio group, a lower alkylsulfinyl group, a lower alkylsulfonyl group, a lower alkylsulfoxide group, a lower alkylcarbonyl group, a methoxymethylthio group, a halogenomethylthio group, a cycloalkylsulfonyl group, a phenyl group, a cycloalkylthio group phenoxy and a cyclohexenyloxy group.

(2) Univalent group of the formula $$\bigcirc_E \text{—} G \text{—} \bigcirc^D \text{—}$$

wherein G denotes a group of the formula $$\overset{O}{\underset{\|}{-C-}},$$

a group of the formula $$\overset{O}{\underset{\|}{-O-C-}},$$

a group of the formula —O—, a group of the formula $$\overset{O}{\underset{\|}{-CH_2-NH-C-}},$$

a group of the formula —CH$_2$—O—, a group of the formula —CH$_2$—SO$_2$—, a group of the formula $$\underset{OH}{\overset{}{-CH-}}$$

or a group of the formula $$\overset{O}{\underset{}{-CH_2-S-}},$$

E denotes a carbon atom or a nitrogen atom, and D has the same meaning as defined in (I).

In the univalent group derived from substituted or unsubstituted phthalimide in the definition of R$^1$, the examples of the preferable substituent include a nitro group, an amino group, a halogen group, a lower alkyl group, a lower alkoxy group, a hydroxy group, a benzoyl group, a phenylcarbonyl group, a phenylcarbonylamino group, a lower alkylcarbonylamino group, a hydroxycarbonyl group, a benzylaminocarbonyl group and a dialkylaminocarbonyl group. The univalent group may be substituted by two or more same or different substituents if necessary.

In the univalent group derived from substituted or unsubstituted quinazolinedione in the definition of R$^1$, the examples of the preferable substituent include a lower alkyl group and a halogen group.

Preparation Method A $$R^1\text{—}X\text{—}Hal + H\text{—}\bigcirc_A\text{—}R^2 \longrightarrow R^1\text{—}X\text{—}\bigcirc_A\text{—}R^2$$
(II)           (III)                    (I)

wherein Hal denotes a halogen atom, and R$^1$, X, R$^2$ and the ring A have the same meaning as defined above.

Namely, a compound of the general formula (II) (wherein Hal denotes a chlorine atom, bromine atom, iodine atom, etc. and among them the bromine atom is most preferable) and a piperidine derivative of the general formula (III) are subjected to a condensation reaction by a conventional method, preferably in the presence of a base such as sodium hydrogencarbonate, sodium carbonate, potassium carbonate or triethylamine, to obtain the final compound (I). In this case, as an organic solvent there is used, for example, benzene, toluene, ethanol, butanol or dimethylformamide (DMF).

Preparation Method B

[In the case where X denotes a group of the formula $$\overset{O}{\underset{\|}{-C-}}\overset{R^3}{\underset{|}{N-}}(CH_2)_n\text{—}$$

in the general formula (I)]

$$R^1\overset{O}{\underset{\|}{-C-}}Hal + H\overset{R^3}{\underset{|}{N-}}(CH_2)_n\text{—}\bigcirc_A\text{—}R^2 \longrightarrow$$
(IV)                    (V)

$$R^1\overset{O}{\underset{\|}{-C-}}\overset{R^3}{\underset{|}{N}}(CH_2)_n\text{—}\bigcirc_A\text{—}R^2$$
(VI)

Namely, an acid halogenide of the general formula (IV) is allowed to react with a piperidine derivative of the general formula (V) in an organic solvent such as chloroform, benzene, toluene, dioxane, tetrahydrofuran or dimethylformamide (DMF), in the presence of a desalting agent such as sodium carbonate, potassium carbonate, sodium hydroxide, potassium hydroxide or triethylamine, with ice-cooling, at room temperature or with heating, to easily obtain the compound (VI), one of the final compounds.

Preparation Method C

[In the case where X denotes a group of the formula —SO$_2$—NH(CH$_2$)$_n$— in the general formula (I)]

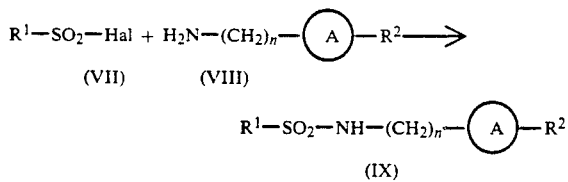

Procedure similar to that of Preparation Method B is used to obtain the compound (IX), one of the final compounds.

Preparation Method D

[In the case where $R^1$ denotes a univalent group derived from imide selected among substituted phthalimide, homophthalimide, pyridinecarboxylic acid imide, pyrazinedicarboxylic acid imide, naphthalenedicarboxylic acid imide, 1,8-naphthalimide, bicyclo [2.2.2] octo-5-ene-2,3-dicarboxylic acid imide and pyromerylimide and X denotes a lower alkylene group in the general formula (I)]

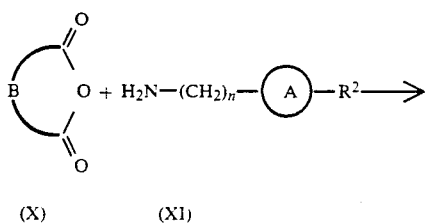

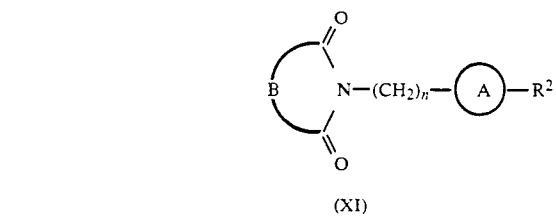

wherein n is an integer of 1 through 7 and B denotes a residue after the removal of a group of the formula

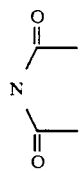

in all the above-defined $R^1$.

Namely, an acid anhydride of the general formula (X) and a piperidine derivative of the general formula (XI) are subjected to a condensation reaction by a conventional method to obtain the compound (XII), one of the object substances.

The reaction is carried out with application of heat in an organic solvent such as, for example, ethanol, butanol, dioxane, dimethylformamide (DMF) or acetic anhydride.

Preparation Method E

[In the case where $R^1$ denotes a univalent group derived from substituted quinazolinedione and X denotes a lower alkylene group]

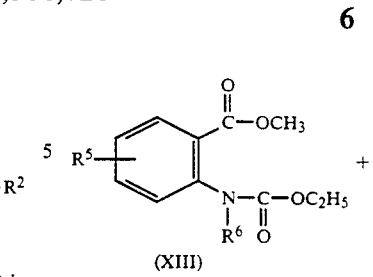

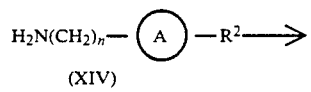

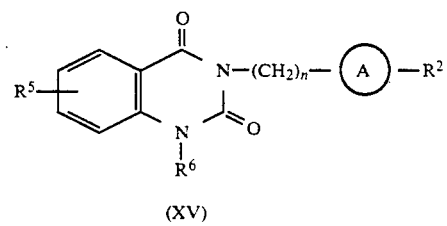

$R^5$ and $R^6$ are hydrogen, or a substituent such as a lower alkyl and a halogen.

Namely, a diester of the general formula (XIII) is allowed to react with a piperidine derivative of the general formula (XIV), with application of heat, in a suitable solvent which does not participate in the reaction or in the absence of the solvent, to obtain the quinazolone compound (XV), one of the object substances.

Preparation Method F

[In the case where $R^1$ denotes a univalent group derived from substituted or unsubstituted benzene and X denotes a group of the formula $-O(CH_2)_n-$ in the general formula (I)]

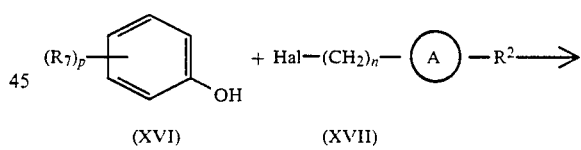

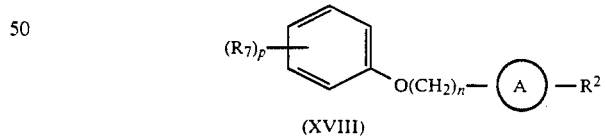

$R^7$ is hydrogen or a phenyl defined above. p is zero or an integer of 1 to 3.

Namely, a phenol derivative of the general formula (XVI) and a halogen compound of the general formula (XVII) are subjected to a condensation reaction by a conventional method to obtain the compound (XVIII), one of the final compounds.

The reaction is carried out in a solvent such as, for example, tetrahydrofuran or dimethylformamide (DMF), in the presence of NaH or NaOH, at room temperature or with heating, thereby obtaining a good result.

Preparation Method G

[In the case where $R^1$ denotes a univalent group derived from substituted or unsubstituted benzene and X denotes a group of the formula $-S(CH_2)_n-$ in the general formula (I)]

$$(R_7)_p-\phenyl-SH \;(XIX) \;+\; Hal-(CH_2)_n-(A)-R^2 \;(XX) \longrightarrow$$

$$(R_7)_p-\phenyl-S(CH_2)_n-(A)-R^2 \;(XXI)$$

Procedure similar to that of Preparation Method F is used to obtain the compound (XXI), one of the object substances.

Preparation Method H $$R^1-X-OH \;(XXII) \;+\; H-(A)-R^2 \;(III) \longrightarrow R^1-X-(A)-R^2 \;(I)$$

wherein $R^1$, X, $R^2$ and the ring A have the same meaning as defined above.

Namely, a compound of the general formula (XXII) and a piperidine derivative of the general formula (III) are subjected to a condensation reaction preferably using a desalting agent such as triethylamine, N-methylmorpholine or N,N'-dimethylaniline to obtain the object substance (I).

In this case, benzene, toluene, tetrahydrofuran, dimethylformamide or dioxane is used as a solvent.

Various attempts have been made to treat for middle-age dementia, senile dementia and so on with medicines. At present, however, there is no medicine which is considered to be drastically effective for the diseases. Considered to be effective at present are anticholinesterase agents (example; physostygumine). The physostygumine, however, suffers disadvantages: action of short duration, strong side effects, and so forth.

Accordingly, the inventors have been making many intensive studies over a long term of years in order to develop medicines having actions of long duration and being high in safety.

As a result, they have discovered that the piperidine derivatives of the general formula (I) can attain the desired end.

Specifically, the compounds of the structural formula (I) according to the invention have the following important features. They have strong and highly-selective antiacetylcholinesterase activities. Furthermore, they increase the amount of acetylcholine in the brain and are effective for the model of retentive disorder. In addition, they have actions of long duration and are high in safety, compared with the physostygumine heretofore in use in the field. Thus, the invention is of great value.

Namely, the compounds of the invention are piperidine derivatives of the following general formula (I) or pharmacologically allowable salts thereof:

$$R^1-X-(A)-R^2 \quad (I)$$

wherein $R^1$ denotes a univalent group derived from one selected among substituted or unsubstituted benzene, pyridine, pyrazine, indole, anthraquinone, quinoline, substituted or unsubstituted phthalimide, homophthalimide, pyridinecarboxylic acid imide, pyridine N-oxide, pyrazinedicarboxylic acid imide, naphthalenedicarboxylic acid imide, substituted or unsubstituted quinazolinedione, 1,8-naphthalimide, bicyclo [2.2.2] octo-5-ene-2,3-dicarboxylic acid imide and pyromerylimide, X denotes a group of the formula $-(CH_2)_n-$, a group of the formula $-O(CH_2)_n-$, a group of the formula $-S(CH_2)_n-$, a group of the formula $-NH(CH_2)_n-$, a group of the formula $-SO_2NH(CH_2)_n-$, a group of the formula $$-NH-\underset{\underset{O}{\|}}{C}-(CH_2)_n-,$$

a group of the formula $$-NH(CH_2)_n-\underset{\underset{O}{\|}}{C}-,$$

a group of the formula $$-\underset{\underset{O}{\|}}{C}-O(CH_2)_n-,$$

a group of the formula $-CH_2NH(CH_2)_n-$, a group of the formula $$-\underset{\underset{O}{\|}}{C}-\underset{\underset{R^3}{|}}{N}-(CH_2)_n-$$

(in all the above formulas, n is an integer of 1 through 7 and $R^3$ represents a lower alkyl group or a benzyl group), a group of the formula $$-O-CH_2CH_2\underset{\underset{CH_3}{|}}{CH}-,$$

a group of the formula $$-O-\underset{\underset{CH_3}{|}}{CH}CH_2CH_2-,$$

a group of the formula $-O-CH_2CH_2CH=$ or a group of the formula $$-O-CH_2-\underset{\underset{OH}{|}}{CH}-CH_2-,$$

the ring A denotes a group of the formula a group of the formula

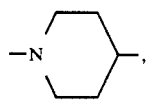

a group of the formula

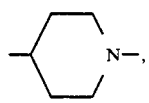

a group of the formula

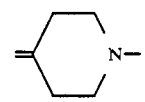

or a group of the formula

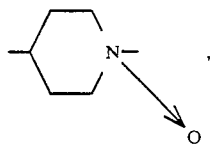

and $R^2$ denotes a hydrogen atom, a lower alkyl group, a substituted or unsubstituted benzyl group, a substituted or unsubstituted benzoyl group, a pyridyl group, a 2-hydroxyethyl group, a pyridylmethyl group or a group of the formula

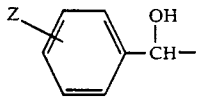

(wherein Z represents a halogen atom).

Therefore the purposes of the invention are to provide a novel compound which is effective for treating various types of dementias and sequelae of cerebrovascular diseases methods for preparation of the compound and a pharmaceutical composition comprising the compound as the effective ingredient.

The pharmacologically acceptable salt, to use in the invention includes for instance an inorganic salt such as hydrochloride, sulfate, hydrobromate or phosphate, and an organic salt with formate, acetate, trifluoroacetate, maleate, tartrate, methanesulfonate, benzenesulfonate or toluenesulfonate.

The compound of the invention is effective for the treatment, prevention, remission and improvement of various types of senile dementia, especially senile dementia of the Alzheimer type or Alzheimer's disease, disturbance of attention, aphasia, hypobulia, emotional disorder, memory disorder, hallucinatory-paranoid state and abnormal behavior, accompanying and following cerebrovasular diseases such as cerebral apoplexy (cerebral hemorrhage, cerebral infraction), sequelae of encephalitis and cerebral palsy.

Further, the compound of the invention has a strong, highly selective anticholinesterase activity and is eventually useful as a medicine based on that activity.

When the compound is used as the medicine, it may be orally or parenterally administered. It is parenterally administered in the form of an intravenous, hypodermic or intramuscular injection or a suppository. It may be administered also in the form of a sublingual tablet. The dose of the administration depends on conditions of the patient, such as age, sex, body weight and sensitivity, the method of the administration such as times and intervals, properties, preparation and kind of the medicine, kind of effective ingredients, and in case another treatment is also effected simultaneously the kind, frequency and intended effects of the treatment. In general, a dose of the administration is about 0.1 to 300 mg, preferably about 1 to 100 mg, for an adult. The administration with the amount is made one to four times a day.

When the compounds of the invention are prepared into medicines, they are prepared into medicines in the form of injections, suppositories, sublingual tablet, tablets, capsules, etc. using ordinary carrier by a conventional method in the technical field of preparation.

In the preparation of injections, pH regulator, buffer, suspending agent, dissolution adjuvant, stabilizer, preservative, etc. are added to the principal ingredient when required, and intravenous, hypodermic and intramuscular injections are prepared by a conventional method. In this case, the injections may be frozen and dried, if necessary, by a conventional method.

Examples of the suspending agent include methyl cellulose, polysorbate 80, hydroxyethyl cellulose, gum arabic, tragacanth powder, carboxymethyl cellulose sodium, polyoxyethylene sorbitan monolaurate, etc.

Examples of the dissolution adjuvant include polyoxyethylene-hardened castor oil, polysorbate 80, amide nicotinate, polyoxyethylene sorbitan monolaurate, castor oil fatty acid ethyl ester, etc.

Examples of the stabilizer include sodium sulfite, sodium metasulfite, ether, etc. Examples of the preservative include methyl paraoxybenzoate, ethyl paraoxybenzoate, sorbic acid, phenol, cresol, chlorocresol, etc.

The representative compounds of the invention will be described hereinafter by way of examples. It goes without saying, however, that the representative compounds are for purpose of help to the understanding of the invention and are not intended as a definition of the limits of the invention.

The values of NMR in the following examples are those in free substances.

EXAMPLE 1

1-benzyl-4-[γ-(4-nitrophenoxy) propyl] piperdine.hydrochloride

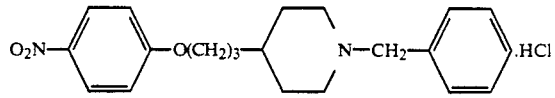

0.8 g of p-nitrophenol and 1.4 g of N-benzyl-4-(γ-bromopropyl)-piperidine are dissolved in 20 ml of dimethylformamide (DMF). To the mixed solution is added, little by little, with stirring at room temperature, 0.3 g of 60% sodium hydride.

Hereafter, the resulting mixture is stirred for 2 hours at room temperature and is further stirred for about 6 hours and 30 minutes at 70° to 80° C. After the solvent is distilled off under reduced pressure, an aqueous chloroform-5% caustic soda solution is added to the residue followed by shaking sufficiently with a separating funnel to separate out a chloroform layer.

The chloroform layer is washed with a saturated saline solution, which is then dried over magnesium sulfate. Chloroform is distilled off under reduced pressure, and the resulting residue is purified using a silica gel column. The distillation is performed using 2% methanol-chloroform. After distilling off the solvent under reduced pressure, the residue is dissolved in ethyl acetate followed by adding a 10% hydrochloric acid-ethyl acetate solution to separate out crystals. Upon recrystallization from ethanol-water-ethyl ether, 1.9 g (yield: 84.1%) of the titled compound having the following physical properties is obtained.

Melting point (°C.): 229–230

Elemental analytical values: $C_{21}H_{26}N_2O_3 \cdot HCl$

|  | C | H | N |
| --- | --- | --- | --- |
| Theoretical value (%) | 64.52 | 6.96 | 7.17 |
| Found value (%) | 64.21 | 7.03 | 7.06 |

EXAMPLE 2

N-[4'-(1'-benzylpiperidine) ethyl]-4-benzylsulfonylbenzamide hydrochloride

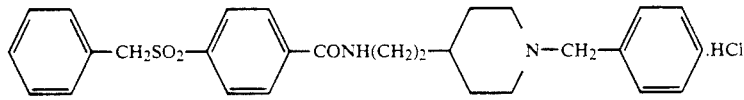

3 g of 1-benzyl-4-aminoethylpiperidine and 2.8 g of triethylamine are added to 100 ml of anhydrous tetrahydrofuran. 4.1 g of 4-benzylsulfonylbenzoylchloride is mixed with 50 ml of anhydrous tetrahydrofuran with ice-cooling and stirring, which is then added dropwise to the above mixed solution for about 20 minutes. The resulting mixture is stirred for about 20 minutes at room temperature and is further refluxed for about 20 minutes. Then, tetrahydrofuran is distilled off under reduced pressure. The resulting residue is purified using a column in a similar manner as in Example 1 and is formed into a hydrochloride by a conventional method to obtain 3.55 g of the titled compound (Yield: 49.4%).

Melting point (°C.): 187–188

Elemental analytical values: $C_{28}H_{32}N_2O_3S \cdot HCl$

|  | C | H | N |
| --- | --- | --- | --- |
| Theoretical value (%) | 65.55 | 6.48 | 5.46 |
| Found value (%) | 64.64 | 6.27 | 5.36 |
| 3/10 (H$_2$O) | 64.86 | 6.53 | 5.46 |

EXAMPLE 3

N-[4'-(1'-benzylpiperidine) ethyl]-4-isonicotinic acid amide hydrochloride

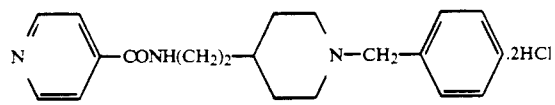

Preparation Example 1

2.4 g of isonicotinic acid chloride hydrochloride is added little by little to 4.4 g of 1-benzyl-4-aminoethyl-piperidine, 5.6 g of potassium carbonate and 50 ml of dioxane while they are cooled with ice and stirred. After the reaction for about 1 hour at room temperature, dioxane is distilled off under reduced pressure. To the resulting residue are added 50 ml of water and 20 ml of a 5% aqueous NaOH solution to alkalify the residue. The alkaline residue is then extracted with chloroform. After washing with water, the resulting chloroform layer is dried over potassium carbonate, and chloroform is distilled off under reduced pressure. The resulting residue is purified with 2% methanol-chloroform-based and 5% methanol-chloroform-based solvents by the use of a silica gel column, and is formed into a hydrochloride using a 10% hydrochloric acid-ethyl acetate solution to obtain 5.1 g of the titled compound (yield: 70.0%).

Preparation Example 2

4.7 g of isonicotinic acid is dissolved in a mixed solution of dimethylformamide-tetrahydrofuran (1/1). To the mixture are added, at −30° to −15° C., 3.85 g of N-methylformalin and 4.13 g of ethyl chlorcarbonate. The resulting mixture is stirred for 5 minutes at −15° C. Dimethylformamide-tetrahydrofuran solution of 8.33 g of N-benzylpiperidylethylamine is added to the reaction solution followed by stirring for 2 hours at 0° C. and then 1 hour at room temperature. After removing a precipitate by filtration, the resulting filtrate is concentrated, and the residue is dissolved in chloroform. After washing with caustic soda and water, the chloroform layer is dried over magnesium sulfate, and chloroform is distilled off. The resulting oily residue is purified using a silica gel chromato to obtain 9.5 g of the titled compound (yield: 77.0%).

NMR (δ value, DMSO): 1.14–2.04 (9H, m), 2.8–2.9 (2H, bd), 3.36–3.56 (2H, m), 3.44 (2H, s), 6.2 (1H, bt), 7.24 (5H, s), 7.54 (2H, m), 8.68 (2H, m)

EXAMPLE 4

N-methyl-N-[4'-(1'-benzylpiperidine)ethyl]-4-benzylsulfonylbenzamide, hydrochloride

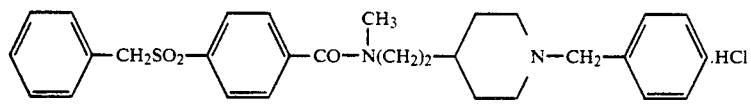

5.9 g of 4-benzylsulfonylbenzoylchloride is added little by little to 4.6 g of 1-benzyl-4-(N'-methylaminoethyl) piperidine, 5 g of triethylamine and 40 ml of chloroform while they are cooled with ice and stirred. After the reaction for 12 hours at room temperature, 20 ml of water and 20 ml of a 5% aqueous NaOH solution are added to the reaction solution followed by shaking sufficiently with a separating funnel to separate out a chloroform layer. After washing with water, the chloroform layer is dried over magnesium sulfate, and chloroform is distilled off under reduced pressure. The resulting residue is purified using a column in a similar manner as in Example 1 and is formed into a hydrochloride. Upon recrystallization from ethanol, 8.2 g of the titled compound is obtained (yield: 78.1%).

Melting point (° C.): 200–201
Elemental analytical values: $C_{29}H_{34}N_2O_3S$

|  | C | H | N |
| --- | --- | --- | --- |
| Theoretical value (%) | 66.08 | 6.69 | 5.31 |
| Found value (%) | 66.12 | 6.67 | 5.21 |

EXAMPLE 5

N-methyl-N-[4'-(1'-benzylpiperidyl) ethyl] isonicotinic acid amide hydrochloride

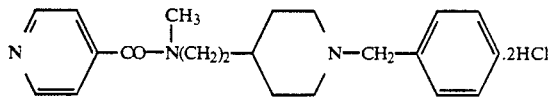

3.48 g of N-benzyl-4-(N'-methylaminoethyl) piperidine and 4.6 g of potassium carbonate are added to a mixed solution of 40 ml of chloroform and 10 ml of water. To the mixture is added, little by little, with ice-cooling and stirring, 3.2 g of isonicotinic acid chloride.hydrochloride.

After stirring for 1 hour at room temperature, 20 ml of water and 10 ml of an aqueous 1N-NaOH solution are added to the reaction solution, and a chloroform layer is separated out. After washing with water, the chloroform layer is dried over magnesium sulfate.

Chloroform is distilled off under reduced pressure to obtain 4.3 g of an oily matter. The oily matter is purified using a silica gel column in a similar manner as in Example 1 and is formed into a hydrochloride.

Upon recrystallization from acetone-ethanol, 4.0 g of the titled compound is obtained (yield: 72.0%).

Elemental analytical values: $C_{21}H_{27}N_3O.2HCl.\frac{1}{2}H_2O$

|  | C | H | N |
| --- | --- | --- | --- |
| Theoretical value (%) | 60.14 | 7.21 | 10.12 |
| Found value (%) | 60.02 | 7.01 | 10.16 |

EXAMPLE 6

N-methyl-N-[4'-(1'-benzylpiperidine)ethyl]-4-cyclopentylsulfonylbenzamide.hydrochloride

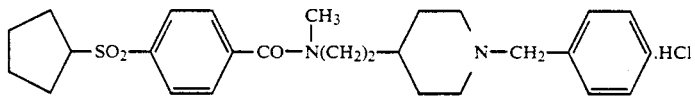

1.1 g of N-benzyl-4-(N'-methylaminoethyl) piperidine and 1.4 g of potassium carbonate are added to a mixed solution of 20 ml of chloroform and 5 ml of water. While stirring the mixture at room temperature, a solution in which 1.16 g of 4-cyclopentylsulfonylchloride is dissolved in 20 ml of chloroform is added dropwise to the mixture. After stirring for 2 hours at room temperature, 10 ml of water and 5 ml of an aqueous 1N-NaOH solution are added to the reaction solution, and a chloroform layer is separated out. After washing with water, the chloroform layer is dried over magnesium sulfate.

Chloroform is distilled off under reduced pressure to obtain a crude product. The crude product is purified using a silica gel column in a similar manner as in Example 1 and is formed into a hydrochloride.

Upon recrystallization from ethanol-ether, 1.9 g of the titled compound is obtained (yield: 80.0%).

Melting point (°C.): 234–236 (decomposition)
Elemental analytical values: $C_{27}H_{36}N_2O_3S.HCl.\frac{1}{2}H_2O$

|  | C | H | N |
| --- | --- | --- | --- |
| Theoretical value (%) | 63.08 | 7.45 | 5.45 |
| Found value (%) | 63.10 | 7.25 | 5.40 |

EXAMPLE 7

N-[2-(N'-benzylpiperidino-4) ethyl]-4-nitrophthalimide.hydrochloride

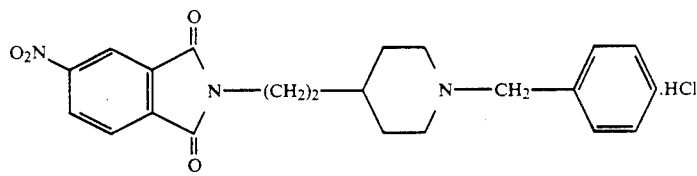

1.0 g of 4-nitro phthalic anhydride and 1.1 g of 4-(2-aminoethyl)-benzylpiperidine are added to 30 ml of dioxane. The resulting mixture is heated and refluxed for 2 hours.

The reaction solution is added with 50 ml of water followed by extracting with chloroform. The resulting chloroform layer is dried over magnesium sulfate, which is then concentrated to dryness under reduced pressure. The resulting residue is purified with a 5% ethanol-chloroform-based solvent by the use of a silica gel column to obtain 1.3 g of the object substance. The object substance is formed into a hydrochloride using a 10% hydrochloric acid-ethyl acetate solution. Upon recrystallization from acetoneisopropyl ether, 0.98 g of the titled compound is obtained (yield: 45.1%).

Melting point (°C.): 224-227

Elemental analytical values: $C_{22}H_{23}N_3O_4.HCl$

|                     | C     | H    | N     |
|---------------------|-------|------|-------|
| Theoretical value (%) | 61.47 | 5.63 | 9.77  |
| Found value (%)     | 61.35 | 5.69 | 10.01 |

EXAMPLE 8

N-[2-(N'-benzylpiperidino-4) ethyl]-2,3-pyrazinedicarboxylic acid imide

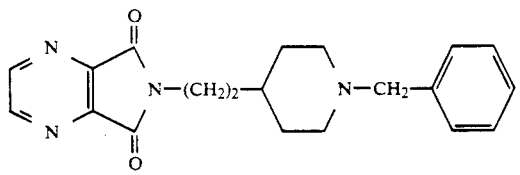

7.5 g of 2,3-pyrazinedicarboxylic anhydride and 12.0 g of 4-(2-aminoethyl)-benzylpiperidine are stirred for 10 minutes at 120° C. to form a brown tar-like mixture. After allowing to stand for cooling, 7 ml of acetic anhydride is added dropwise to the brown tar-like mixture at 80° C. followed by stirring for about 30 minutes at 100° C. The resulting tar-like substance is added with and dissolved in 20 ml of chloroform and is purified using a silica gel column in a similar manner as in Example 1. Since the object substance is not well separated out, the above tar-like substance is further purified by distillation with benzene and a 10% ethanol-benzene-based solvent, to obtain 5.9 g of the object compound as a yellow-brown oily matter (yield: 33.6%).

NMR (δ value, DMSO): 1.27-2.02 (9H, m), 2.8-2.9 (2H, bd), 3.46 (2H, s), 3.82 (2H, t), 7.26 (5H, s), 8.87 (2H, s)

EXAMPLE 9

N-[2-(N'-benzylpiperidino-4) ethyl]-1,8-naphthalimide

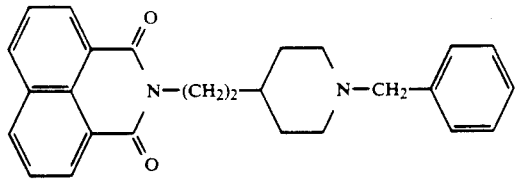

2 g of 1,8-naphthalic anhydride and 2.2 g of 4-(2-aminoethyl) benzylpiperidine are heated and refluxed in a solvent of n-butanol for 6 hours.

After allowing to stand for cooling, 50 ml of water is added to the reaction solution followed by extracting with chloroform. The resulting chloroform layer is dried over potassium carbonate, which is then concentrated to dryness under reduced pressure.

The oily residue thus obtained is purified with chloroform as a distilling solvent by the use of a silica gel column. The purified substance is formed into a hydrochloride using a 10% hydrochloric acid-ethanol solution. Upon recrystallization from ethanol-methanol, 2.0 g of the object compound is obtained (yield: 46%).

NMR (δ value, DMSO): 2.84 (2H, d), 3.45 (2H, s), 4.4 (2H, q), 7.24 (5H, s), 7.4 (2H, q), 8.1 (2H, dd), 8.5 (2H, dd)

EXAMPLE 10

3-[2-(1-benzyl-4-piperidino) ethyl]-2,4-(1H,3H)-quinazolidione.hydrochloride

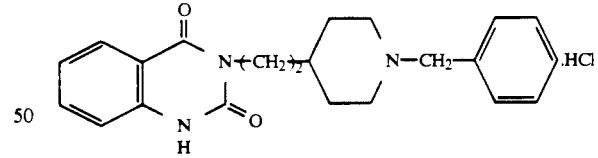

A mixture of 50 g of 2-[(ethoxycarbonyl) amino] benzoic acid methyl and 49 g of 4-(2-aminoethyl)benzylpiperidine is heated to 190° to 200° C. with stirring, and methanol and ethanol formed are distilled off.

After heating and stirring for about 6 hours, the mixture is purified using a silica gel column in a similar manner as in Example 1 and is formed into a hydrochloride.

Upon recrystallization from ethanol-water, 13.3 g of the titled compound is obtained (yield: 14.8%).

Melting point (°C.): 208-210

Elemental analytical values: $C_{22}H_{25}N_3O_2.HCl$

|                       | C     | H    | N     |
|-----------------------|-------|------|-------|
| Theoretical value (%) | 66.07 | 6.55 | 10.51 |

-continued
|  | C | H | N |
|---|---|---|---|
| Found value (%) | 66.02 | 6.64 | 10.75 |
EXAMPLES 11 TO 137
Compounds prepared using similar procedures as in Examples 1 to 10 are shown in Table 1 and Table 2.
The compounds shown in Tables 1 and 2 are represented by the formula
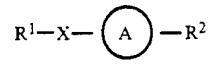

TABLE 1

R¹—X—(A)—R²

| Example | R¹ | X | (A) | R² | Melting point (°C.) | Solvent for recrystallization | Molecular formula | Elemental analytical value (%) Upper column: Theoretical value (%) Bottom column: Found value (%) C H N | | | Preparation method |
|---|---|---|---|---|---|---|---|---|---|---|---|
| 11 |  | —O(CH₂)₃— |  |  | 137~138.5 | EtOH-IPE | C₂₀H₂₄N₂O₃·½H₂O·HCl | 62.98 62.85 | 6.74 6.65 | 7.34 7.16 | A |
| 12 |  | —O(CH₂)₃— |  | H | 203~204 | EtOH | C₁₂H₁₈N₂O₃·HCl | 54.44 54.38 | 6.68 6.64 | 9.77 9.57 | A |
| 13 |  | —O(CH₂)₃— |  |  | 100~101 | EtOH-IPE | C₁₂H₂₆N₂O₄ | 68.73 68.50 | 7.34 7.61 | 7.29 7.38 | A |
| 14 |  | —O(CH₂)₃— |  |  | 170~176 | EtOH-IPE | C₁₂H₂₇N₂O₃F·HCl | 58.08 58.01 | 6.20 6.11 | 6.16 6.22 | A |
| 15 |  | —O(CH₂)₃— |  |  | 179~180 | EtOH | C₂₇H₃₀N₂O₃·HCl | 69.44 69.51 | 6.69 6.72 | 6.06 6.11 | E |
| 16 |  | —O(CH₂)₃— |  |  | 135~137 | Actone IPE | C₂₁H₂₈N₂O₃·HCl | 68.21 68.01 | 5.93 6.02 | 5.68 5.58 | E |

TABLE 1-continued $R^1-X-\text{(A)}-R^2$

| Example | R¹ | X | (A) | R² | Melting point (°C.) | Solvent for recrystallization | Molecular formula | Elemental analytical value (%) Upper column: Theoretical value (%) Bottom column: Found value (%) C H N | | | Preparation method |
|---|---|---|---|---|---|---|---|---|---|---|---|
| 17 |  | —OCH₂CH₃CH— | 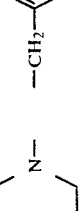 | —CH₂— | 214~217 | EtOH-H₂O | C₂₁H₂₄N₂O₃·HCl.½H₂O | 64.12 64.12 | 6.53 6.58 | 7.12 7.24 | E |
| 18 |  | —O(CH₂)₃— | 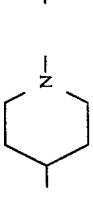 | —CH₂— | 159~161 | EtOH-IPE | C₂₁H₃₁N₂O₄F.HCl | 62.68 62.39 | 6.75 6.69 | 5.85 5.99 | A |
| 19 |  | —CONH(CH₂)₂— |  | —CH₂— | 107~113 | EtOH Ether | C₂₁H₂₈N₂O₂S.HCl | 62.77 62.71 | 6.94 6.91 | 6.65 6.59 | B |
| 20 | 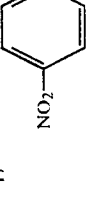 | —CONH(CH₂)₂— |  | —CH₂— | 186~188 | EtOH Ether | C₂₂H₃₀N₂O₂.HCl | 66.26 66.15 | 7.01 7.18 | 6.72 6.61 | B |
| 21 |  | —CONH(CH₂)₂— |  | —CH₂— | 156~158 | — | C₂₂H₂₉N₂O₄.HCl | 63.80 63.74 | 6.75 6.78 | 6.47 6.61 | B |
| 22 |  | —CONH(CH₂)₂— |  | —CH₂— | 166~168 | — | C₂₈H₃₂N₂O₂.HCl (2/5 H₂O) | 78.47 76.57 76.54 | 7.53 7.58 7.62 | 6.54 6.24 6.38 | B |

TABLE 1-continued $R^1-X-\underset{A}{\bigcirc}-R^2$

| Example | R¹ | X | A | R² | Melting point (°C.) | Solvent for recrystal-lization | Molecular formula | Elemental analytical value (%) Upper column: Theoretical value (%) Bottom column: Found value (%) | | | Preparation method |
|---|---|---|---|---|---|---|---|---|---|---|---|
| | | | | | | | | C | H | N | |
| 23 | 4-methylphenyl-SO₂-cyclopentyl | —CONH(CH₂)₂— | piperidine | —CH₂-phenyl | 245~247 (Decomposition) | EtOH Ether | C₂₄H₁₄N₂O₂S· HCl·½H₂O | 62.45 61.99 | 7.26 7.03 | 5.60 5.68 | B |
| 24 | cyclohexyl-CH₂- | —CONH(CH₂)₂— | piperidine | —CH₂-phenyl | 182~184 | EtOH | C₂₁H₂₄N₂O₂· HCl | 68.29 68.33 | 7.03 7.16 | 7.24 7.41 | B |
| 25 | anthraquinonyl | —CONH(CH₂)₂— | piperidine | —CH₂-phenyl | 255~257 (Decomposition) | EtOH | C₂₂H₂₆N₂O₂· HCl | 71.23 71.51 | 5.98 5.80 | 5.73 5.81 | B |
| 26 | 4-methylphenyl-CH₂NHC(O)-phenyl | —CONH(CH₂)₂— | piperidine | —CH₂-phenyl | 225~226 | EtOH | C₂₇H₃₃N₃O₂· HCl | 70.79 70.91 | 6.96 7.03 | 8.54 8.61 | B |
| 27 | 2-methylindolyl | —CONH(CH₂)₂— | piperidine | —CH₂-phenyl | 234~235 | EtOH Ether | C₁₂H₁₇N₂O· HCl | 69.42 69.31 | 7.09 7.00 | 10.56 10.46 | B |
| 28 | phenyl | —CON(CH₃)(CH₂)₂— | piperidine | —CH₂-phenyl | 183~184 | — | C₁₂H₂₈N₂O· HCl | 70.85 70.87 | 7.84 7.75 | 7.51 7.54 | B |

TABLE 1-continued

R¹—X—(A)—R²

| Example | R¹ | X | (A) | R² | Melting point (°C.) | Solvent for recrystallization | Molecular formula | Elemental analytical value (%) Upper column: Found value (%) Bottom column: Theoretical value (%) C / H / N | Preparation method |
|---|---|---|---|---|---|---|---|---|---|
| 29 | CH₂S—C₆H₄— (p-methylthiophenyl) | —CON(CH₂)₂— with CH₃ | piperidine-N,4-yl | —CH₂—C₆H₅ | 174~175 | — | $C_{12}H_{24}N_2OS \cdot HCl$ | 65.93 7.46 6.69 / 65.98 7.44 6.65 | B |
| 30 | CH₂CO—C₆H₄— (p-acetylphenyl) | —CON(CH₂)₂— with CH₃ | piperidine-N,4-yl | —CH₂—C₆H₅ | 164~165 | — | $C_{24}H_{30}N_2O_2 \cdot HCl$ | 69.47 7.53 6.75 / 69.34 7.53 6.68 | B |
| 31 | (CH₃)₂CH-CO-C₆H₄— | —CON(CH₂)₂— with CH₃ | piperidine-N,4-yl | —CH₂—C₆H₅ | 185~186 | — | $C_{26}H_{24}N_2O_2 \cdot HCl$ | 70.49 7.96 6.32 / 70.18 7.83 6.54 | B |
| 32 | biphenyl-4-yl | —CON(CH₂)₂— with CH₃ | piperidine-N,4-yl | —CH₂—C₆H₅ | 195~196 | — | $C_{22}H_{32}N_2O \cdot HCl$ | 74.90 7.41 6.24 / 74.60 7.46 6.28 | B |
| 33 | 2-methylanthraquinonyl | —CON(CH₂)₂— with CH₃ | piperidine-N,4-yl | —CH₂—C₆H₅ | 235~236 | EtOH | $C_{14}H_{16}N_2O_2 \cdot HCl \cdot \frac{1}{2}H_2O$ | 70.37 6.30 5.47 / 70.12 6.23 5.28 | B |
| 34 | 4-methylpyridine N-oxide | —CONH(CH₂)₂— | piperidine-N,4-yl | —CH₂—C₆H₅ | 119~123 | EtOH / IPE | $C_{14}H_{11}N_2O_2 \cdot HCl$ | 63.91 6.97 11.18 / 63.88 6.98 11.16 | B |

TABLE 1-continued $$R^1-X-\underset{(A)}{\bigcirc}-R^2$$

| Example | R¹ | X | A | R² | Melting point (°C.) | Solvent for recrystallization | Molecular formula | Elemental analytical value (%) Upper column: Theoretical value (%) Bottom column: Found value (%) C / H / N | Preparation method |
|---|---|---|---|---|---|---|---|---|---|
| 35 | 4-(CH₃CO)-C₆H₄- | −CON(CH₂)₂− with C₂H₅ on N | piperidine (N-) | −CH₂−C₆H₅ | 203~204 | — | C₁₁H₃₂N₂O₂·HCl | 70.00 7.75 6.53 / 70.00 7.80 6.47 | B |
| 36 | 4-pyridyl | −CONH(CH₂)₂− | piperidine (N-) | −CH₂−C₆H₅ | 161~164 | — | C₁₄H₂₁N₂O | 67.98 8.56 16.99 / 67.91 8.48 16.76 | B |
| 37 | 4-(C₆H₅-CH₂NHCO)-C₆H₄- | −CONH(CH₂)₂− | piperidine (N-) | −CH₂−(4-pyridyl) | 106~110 | MeOH Ether | C₁₈H₂₁N₄O₂·2HCl | 63.51 6.47 10.58 / 63.35 6.59 10.66 | B |
| 38 | 2-pyridyl with CH₂NHC=O-C₆H₄- | −CONH(CH₂)₂− | piperidine (N-) | −CH₂−(4-pyridyl) | 127~129 | MeOH IPE | C₂₁H₂₁N₃O₂·3HCl | 58.09 5.92 12.09 / 58.18 5.99 11.81 | B |
| 39 | C₆H₅-CH₂S(O)-C₆H₄- | −CON(CH₂)₂− with CH₃ on N | piperidine (N-) | −CH₂−(4-pyridyl) | 118~122 | Acetone IPE | C₂₇H₂₁N₃O₂S·2HCl | 60.66 6.22 7.86 / 60.88 6.01 7.59 | B |
| 40 | C₆H₅-CH₂SO₂-C₆H₄- | −CONH(CH₂)₂− | piperidine (N-) | −CH₂−(4-OCH₃-C₆H₄) | 135~136 | Acetone n-Hexane | C₃₄H₃₄N₃O₄S | 69.20 6.97 5.38 / 68.89 6.87 5.09 | B |

TABLE 1-continued

R¹—X—(A)—R²

| Example | R¹ | X | A | R² | Melting point (°C.) | Solvent for recrystallization | Molecular formula | Elemental analytical value (%) Upper column: Theoretical value (%) Bottom column: Found value (%) C H N | | | Preparation method |
|---|---|---|---|---|---|---|---|---|---|---|---|
| 41 | CH₂SO₂-C₆H₄- | $\underset{-CON(CH_2)_2-}{CH_3}$ | piperidine (N-) | -CH₂-C₆H₄-OH (4-) | 176~178 | — | C₁₉H₁₄N₃O₄S | 68.75 68.66 | 6.76 6.68 | 5.53 5.27 | B |
| 42 | CH₂SO₂-C₆H₄- | $\underset{-CON(CH_2)_2-}{CH_3}$ | piperidine (N-) | -H | 149~151 | MeOH IPE | C₂₁H₂₁N₃O₂S | 65.97 65.92 | 7.05 6.95 | 6.99 6.90 | B |
| 43 | CH₂SO₂-C₆H₄- | $\underset{-CON(CH_2)_2-}{CH_3}$ | piperidine N-oxide | -CH₂-C₆H₅ | 163~164 | EtOH IPE | C₂₉H₃₄N₃O₄S | 68.75 68.46 | 6.76 6.78 | 5.53 5.27 | B |
| 44 | C₆H₅-CH₂NHC(O)-C₆H₄- | $\underset{-CON(CH_2)_2-}{CH_3}$ | piperidine (N-) | -CH₂CH₂OH | 114~116 | MeOH IPE | C₃₀H₃₁N₃O₃·HCl | 69.55 69.49 | 6.23 6.33 | 8.11 8.19 | B |
| 45 | 4-NO₂-C₆H₄- | -SO₂NH(CH₂)₂- | piperidine (N-) | -CH₂-C₆H₅ | 122~123 | EtOH | C₁₄H₂₅N₃O₄S | 61.68 61.57 | 6.47 6.33 | 7.19 7.02 | B |
| 46 | 5-nitrophthalimide | — | piperidine (N-) | -CH₂-C₆H₅ | 254~255 | EtOH | C₁₉H₁₇N₃O₄·HCl | 59.70 59.99 | 5.02 5.13 | 10.46 10.41 | C |

TABLE 1-continued

R¹—X—(A)—R²

| Example | R¹ | X | A | R² | Melting point (°C.) | Solvent for recrystallization | Molecular formula | Elemental analytical value (%) Upper column: Theoretical value (%) Bottom column: Found value (%) C H N | Preparation method |
|---|---|---|---|---|---|---|---|---|---|
| 47 | 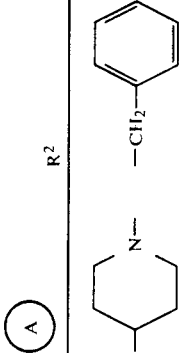 | —(CH₂)₂— | piperidine | —CH₂—C₆H₅ | 177~179 | EtOH Ether | C₂₁H₁₃N₃O₄·HCl | 61.47 5.63 9.77<br>61.59 5.66 8.51 | C |
| 48 | 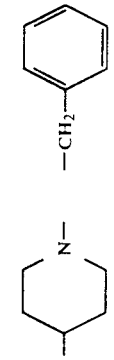 | —(CH₂)₂— | piperidine | —CH₂—C₆H₅ | 116~118 | MeOH IPE | C₁₁H₁₂N₃O₄·HCl | 61.47 5.63 9.77<br>61.30 5.61 9.87 | C |
| 49 | 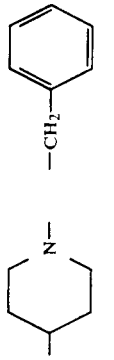 | —(CH₂)₂— | piperidine | —CH₂—C₆H₅ | 246~248 (Decomposition) | EtOH Ether | C₁₉H₂₉N₃O₁·HCl | 69.11 6.00 8.34<br>68.96 6.12 8.39 | C |
| 50 | 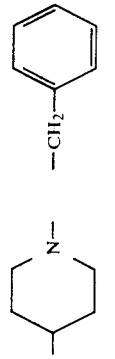 | —(CH₂)₂— | piperidine | —CH₂—C₆H₅ | 238~239 (Decomposition) | MeOH Ether | C₁₄H₁₇N₃O₃·HCl | 65.22 6.39 9.51<br>65.43 6.28 9.60 | C |

TABLE 1-continued

R¹—X—(A)—R²

| Example | R¹ | X | (A) | R² | Melting point (°C.) | Solvent for recrystallization | Molecular formula | Elemental analytical value (%) Upper column: Found value (%) Bottom column: Theoretical value (%) C H N | Preparation method |
|---|---|---|---|---|---|---|---|---|---|
| 51 | ![phthalimide with CH₂NHC(=O)C₆H₅] | —(CH₂)₂— | ![piperidine] | —CH₂—C₆H₅ | 227~228 (Decomposition) | EtOH Ether | C₃₀H₃₁N₃O₃·HCl | 69.55 6.23 8.11<br>69.29 6.34 8.08 | C |
| 52 | ![phthalimide with C(=O)N(C₂H₅)₂] | —(CH₂)₂— | ![piperidine] | —CH₂—C₆H₅ | 161~164 | EtOH Ether | C₁₇H₂₂N₃O₂·HCl | 66.80 7.27 8.66<br>66.85 7.05 8.64 | C |
| 53 | ![phthalimide with C(=O)C₆H₅] | —(CH₂)₂— | ![piperidine] | —CH₂—C₆H₅ | 162~163 | — | C₁₇H₁₄N₃O₂·HCl | 71.22 5.98 5.73<br>70.98 5.96 5.79 | C |
| 54 | ![phthalimide with CH₂O—] | —(CH₂)₂— | ![piperidine] | —CH₂—C₆H₅ | 221~222 (Decomposition) | EtOH IPE | C₁₂H₁₄N₁O₂·HCl | 66.57 6.56 6.75<br>66.42 6.59 6.67 | C |

TABLE 1-continued $R^1-X-\text{(A)}-R^2$

| Example | $R^1$ | X | (A) | $R^2$ | Melting point (°C.) | Solvent for recrystallization | Molecular formula | Elemental analytical value (%) Upper column: Theoretical value (%) Bottom column: Found value (%) C H N | | | Preparation method |
|---|---|---|---|---|---|---|---|---|---|---|---|
| 55 | 4-HO-phthalimide | $-(CH_2)_2-$ | 4-piperidine | $-CH_2-$phenyl | 221~224 (Decomposition) | EtOH IPE | $C_{11}H_{14}N_1O_2 \cdot HCl$ | 65.91 6.29 6.99 / 65.77 6.34 6.69 | | | C |
| 56 | 4-CH₃O-5-Cl-phthalimide | $-(CH_2)_2-$ | 4-piperidine | $-CH_2-$phenyl | 222~223 (Decomposition) | EtOH Ether | $C_{13}H_{15}N_1O_2Cl \cdot HCl$ | 61.47 5.83 6.24 / 61.33 5.92 6.31 | | | C |
| 57 | naphthalimide | $-(CH_2)_2-$ | 4-piperidine | $-CH_2-$phenyl | 235~236 (Decomposition) | EtOH | $C_{14}H_{24}N_1O_2 \cdot HCl$ | 71.80 6.26 6.44 / 71.49 6.17 6.41 | | | C |
| 58 | pyridine-dicarboximide | $-(CH_2)_2-$ | 4-piperidine | $-CH_2-$phenyl | 178~181 | Acetone IPE | $C_{11}H_{21}N_3O_2 \cdot 2HCl$ | 61.77 6.17 6.86 / 61.46 6.35 7.17 | | | C |

TABLE 1-continued $R^1-X-\underset{\text{(A)}}{\bigcirc}-R^2$

| Example | R¹ | X | A | R² | Melting point (°C.) | Solvent for recrystallization | Molecular formula | Elemental analytical value (%) Upper column: Found value (%) Bottom column: Theoretical value (%) | | | Preparation method |
|---|---|---|---|---|---|---|---|---|---|---|---|
| | | | | | | | | C | H | N | |
| 59 | (pyridine-fused succinimide) | —(CH₂)₂— | (4-methylpiperidine) | —CH₂-phenyl | 161~163 | Acetone IPE | C₂₁H₁₂N₃O₂· 2HCl | 61.77 61.51 | 6.17 6.22 | 6.86 7.21 | C |
| 60 | (isoquinoline-1,3-dione) | —(CH₂)₂— | (4-methylpiperidine) | —CH₂-phenyl | 210~214 (Decomposition) | EtOH IPE | C₁₂H₁₄N₃O₂· HCl | 69.25 68.96 | 6.82 6.80 | 7.02 7.01 | C |
| 61 | (norbornene dicarboximide) | —(CH₂)₂— | (4-methylpiperidine) | —CH₂-phenyl | 266~268 | EtOH MeOH | C₁₄H₂₀N₃O₂· HCl | 69.47 69.31 | 7.53 7.46 | 6.72 6.63 | C |
| 62 | (4-nitrophthalimide) | —(CH₂)₂— | (4-methylpiperidine) | —CH₂-phenyl | 1986~204 (Decomposition) | CHCl₃ Ether | C₁₃H₁₁N₃O₄· HCl | 62.23 61.94 | 5.90 5.95 | 9.47 9.15 | C |

TABLE 1-continued $R^1-X-\text{(A)}-R^2$

| Example | $R^1$ | X | (A) | $R^2$ | Melting point (°C.) | Solvent for recrystallization | Molecular formula | Elemental analytical value (%) Upper column: Theoretical value (%) Bottom column: Found value (%) | | | Preparation method |
|---|---|---|---|---|---|---|---|---|---|---|---|
| | | | | | | | | C | H | N | |
| 63 | pyridine-fused succinimide | —(CH$_2$)$_2$— | piperidine | —CH$_2$-phenyl | 184~188 (Decomposition) | EtOH Ether | C$_{17}$H$_{15}$N$_3$O$_2$·2HCl | 60.55 60.21 | 6.24 6.11 | 9.63 9.57 | C |
| 64 | 5-nitrophthalimide | —(CH$_2$)$_2$— | piperidine | —CH$_2$ | 256~258 (Decomposition) | EtOH IPE | C$_{14}$H$_{19}$N$_3$O$_4$·HCl | 54.31 54.29 | 5.70 5.71 | 11.88 11.81 | C |
| 65 | 5-nitrophthalimide | —(CH$_2$)$_2$— | piperidine | —CH$_2$-C$_6$H$_4$-OCH$_3$ | 205~206 | — | C$_{12}$H$_{15}$N$_3$O$_5$·HCl | 60.06 60.09 | 5.76 5.73 | 9.14 9.08 | C |
| 66 | 5-nitrophthalimide | —(CH$_2$)$_2$— | piperidine | —CH$_2$-C$_6$H$_4$-Cl | 229~231 | — | C$_{11}$H$_{11}$N$_3$O$_4$Cl·HCl | 56.91 56.91 | 4.99 5.02 | 9.05 9.03 | C |
| 67 | phenyl | —CH$_2$NH(CH$_2$)$_2$— | piperidine | —CH$_2$-phenyl | 273~276 (Decomposition) | EtOH Ether | C$_{11}$H$_{18}$N$_3$·2HCl | 66.13 65.73 | 7.93 7.79 | 7.35 7.28 | A |

TABLE 1-continued $$R^1-X-\underset{(A)}{\bigcirc}-R^2$$

| Example | R¹ | X | A | R² | Melting point (°C.) | Solvent for recrystallization | Molecular formula | Elemental analytical value (%) Upper column: Theoretical value (%) Bottom column: Found value (%) C / H / N | Preparation method |
|---|---|---|---|---|---|---|---|---|---|
| 68 | (2-acetamido-4-chlorobenzoyl, N-linked) | —(CH₂)₂— | 4-methylpiperidine (N-linked) | —CH₂-phenyl | 212~213 | EtOH | C₁₂H₁₄N₃O₂Cl·HCl | 60.83 5.80 9.67 / 60.61 5.93 9.76 | D |
| 69 | (2-(N-methylacetamido)benzoyl, N-linked) | —(CH₂)₂— | 4-methylpiperidine (N-linked) | —CH₂-phenyl | 221~223 | EtOH Ether | C₁₂H₁₇N₃O₂·HCl | 66.74 6.82 10.15 / 66.92 6.71 10.04 | D |

TABLE 2

R¹—X—(A)—R²

| Example | R¹ | X | (A) | R² | Molecular formula | H¹-NMR(CDCl₃, ppm) | Preparation method |
|---|---|---|---|---|---|---|---|
| 70 | phenyl | —CONH(CH₂)₂— | piperidine (N, 4-) | —CH₂—phenyl | $C_{21}H_{26}N_3O \cdot HCl$ | 1.16~2.04(9H, m), 2.7~2.96(2H, d), 3.28~3.56(4H, m), 6.0(1H, s), 7.2~7.76(10H, m) | B |
| 71 | 4-NO₂-phenyl | —CONH(CH₂)₂— | piperidine | —CH₂—phenyl | $C_{21}H_{26}N_3O_2$ | 1.08~2.12(9H, m), 2.84~2.96(2H, d), 3.38~3.6(2H, m), 3.52(2H, s), 6.40(1H, bt), 7.3(5H, s), 7.9(2H, d), 8.24(2H, d) | B |
| 72 | 4-CH₃-phenyl | —CONH(CH₂)₂— | piperidine | —CH₂—phenyl | $C_{21}H_{26}N_3O$ | 1.1~2.06(9H, m), 2.8~2.9(2H, bd), 3.32~3.56(4H, sjm), 6.36(1H, t), 7.26(5H, s), 7.64(2H, d), 7.84(2H, d) | B |
| 73 | 3-CH₃O-phenyl | —CONH(CH₂)₂— | piperidine | —CH₂—phenyl | $C_{21}H_{26}N_3O_2$ | 1.24~2.03(9H, m), 2.8~2.86(2H, d), 3.26~3.48(2H, m), 3.46(2H, s), 3.8(3H, s), 6.14(1H, bt), 6.9~7.3(9H, m) | B |
| 74 | 2,3,4-tri(CH₃O)-phenyl | —CONH(CH₂)₂— | piperidine | —CH₂—phenyl | $C_{24}H_{32}N_3O_4$ | 1.2~2.04(9H, m), 2.76~2.88(2H, bd), 3.35~3.58(4H, slt), 3.84(9H, s), 6.30(1H, bt), 7.0(2H, s), 7.28(5H, s) | B |
| 75 | 4-Cl-phenyl | —CONH(CH₂)₂— | piperidine | —CH₂—phenyl | $C_{21}H_{25}N_3OCl$ | 2.9(2H, d), 3.45(3H, s, d), 6.26(1H, bt), 7.26(5H, s), 7.3(2H, d), 7.7(2H, d) | B |

TABLE 2-continued

R¹—X—(A)—R²

| Example | R¹ | X | (A) | R² | Molecular formula | ¹H NMR | Preparation method |
|---|---|---|---|---|---|---|---|
| 76 |  (3,5-bis(CH₂O)phenyl) | —CONH(CH₂)₂— |  (4-piperidinyl) | —CH₂—  (phenyl) | $C_{22}H_{14}N_3O_4$ | 2.9(2H, d), 3.46(3H, s, d), 3.78(6H, s), 6.12(1H, bt), 6.5(1H, t), 6.82(2H, d), 7.26(5H, s) | B |
| 77 |  (4-(CH₃)₂N-phenyl) | —CONH(CH₂)₂— |  | —CH₂—  | $C_{22}H_{31}N_3O$ | 2.7(2H, d), 2.8(6H, s), 3.34(2H, s), 6.46(2H, d), 6.5(1H, d), 7.12(5H, s), 7.59(2H, d) | B |
| 78 |  (methylenedioxyphenyl) | —CONH(CH₂)₂— |  | —CH₂—  | $C_{22}H_{26}N_3O_2$ | 1.1~2.0(9H, m), 2.76~2.96(2H, bd), 3.26~3.48(4H, m), 5.94(2H, s), 6.32(1H, bt), 6.72(1H, d), 7.24(2H, s) | B |
| 79 |  (4-CH₃S-phenyl) | —CONH(CH₂)₂— |  | —CH₂—  | $C_{22}H_{18}N_3OS$ | 1.02~2.04(9H, m), 2.8~2.9(2H, bd), 2.8~2.9(2H, bd), 3.2~3.5(4H, slm), 6.26(1H, bt), 7.18(2H, d), 7.28(5H, s), 7.64(2H, d) | B |
| 80 |  (4-CH₃SO₂-phenyl) | —CONH(CH₂)₂— |  | —CH₂—  | $C_{22}H_{18}N_3O_2S$ | 1.12~2.06(9H, m), 2.8~2.9(2H, bd), 3.04(3H, s), 3.36~3.58(2H, m), 3.48(2H, s), 6.3(1H, bt), 7.26(5H, s), 7.9(4H, s) | B |
| 81 |  (4-CF₃-phenyl) | —CONH(CH₂)₂— | (piperidine) | —CH₂—(phenyl) | $C_{22}H_{25}N_3OF_2$ | 1.3~2.08(9H, m), 2.86(2H, bd), 3.46(2H, s), 6.0(1H, bs), 7.16(5H, s), 7.64(2H, d), 7.92(2H, d) | B |
| 82 |  (4-CHO-phenyl) | —CONH(CH₂)₂— | (piperidine) | —CH₂—(phenyl) | $C_{22}H_{24}N_3O_2$ | 1.2~2.20(9H, m), 2.90(2H, bd), 3.42(3H, m), 3.60(2H, s), 7.30(5H, s), 7.92(4H, s), 10.02(1H, s) | B |

TABLE 2-continued

R¹—X—(A)—R²

| Example | R¹ | X | (A) | R² | Molecular formula | ¹H NMR | Preparation method |
|---|---|---|---|---|---|---|---|
| 83 | 4-HO-C₆H₄- | —CONH(CH₂)₂— | piperidine (N-, 4-) | —CH₂—C₆H₅ | C₂₂H₂₄N₃O₂ | 1.2~2.04(9H, m), 2.84(2H, bd), 3.30(2H, m), 3.46(2H, s), 6.52(1H, bs), 6.66(2H, d), 7.22(5H, s), 7.52(2H, d), 8.30(1H, s) | B |
| 84 | 4-CH₃O-C₆H₄-C₆H₄- | —CONH(CH₂)₂— | piperidine | —CH₂—C₆H₅ | C₂₂H₃₁N₃O₂ | 1.1~2.04(9H, m), 2.84(2H, bd), 3.44(4H, slm), 5.06(2H, m), 6.00(1H, bt), 6.92(2H, d), 7.14~7.44(10H, m), 7.68(2H, d) | B |
| 85 | 4-CH₃-C₆H₄-CH(C₂H₅)(C₂H₅)- [actually (C₂H₅)₂CH-] | —CONH(CH₂)₂— | piperidine | —CH₂—C₆H₅ | C₂₂H₂₁N₃O₂ | 1.06~2.04(15H, m), 2.8(2H, bd), 3.10~3.60(8H, slm), 6.96(1H, bl), 7.22(7H, slt), 7.66(2H, d) | B |
| 86 | 4-CH₃-C₆H₄-O-cyclohexenyl | —CONH(CH₂)₂— | piperidine | —CH₂—C₆H₅ | C₂₇H₃₄N₃O₂ | 1.1~2.1(15H, m), 2.76~2.88(2H, bd), 3.3~3.5(2H, m), 3.44(2H, s), 4.8(1H, m), 5.7~6.04(2H, m), 6.88(2H, d), 7.20(5H, d), 7.64(2H, d) | B |
| 87 | 4-CH₃CNH-C₆H₄- (CH₃C(O)NH-) | —CONH(CH₂)₂— | piperidine | —CH₂—C₆H₅ | C₂₃H₁₉N₃O₂ | 1.3~2.0(7H, m), 2.7~3.4(6H, m), 4.14~4.36(5H, m), 7.3~8.04(9H, m), 8.40(1H, m), 10.00(1H, m) | B |
| 88 | 4-CH₃S-C₆H₄-C₆H₄- | —CONH(CH₂)₂— | piperidine | —CH₂—C₆H₅ | C₂₈H₃₁N₃OS | 1.0~1.98(9H, m), 2.6~2.86(2H, m), 3.08~3.5(, mls), 4.28(2H, s), 7.2~7.4(12H, m), 7.7(2H, d), 8.32(1H, bt) | B |
| 89 | 4-CH₃-C₆H₄-S-cyclopentyl | —CONH(CH₂)₂— | piperidine | —CH₂—C₆H₅ | C₂₁H₃₄N₃OS | 8.9~2.3(17H, m), 3.08~3.2(2H, bd), 2.5~2.78(5H, m), 3.1(1H, m), 7.06~7.9(9H, m) | B |

TABLE 2-continued

| Example | R¹ | X | A | R² | Molecular formula | NMR | Preparation method |
|---|---|---|---|---|---|---|---|
| 90 | 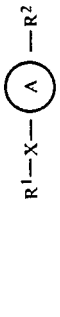 | —CONH(CH₂)₂— | 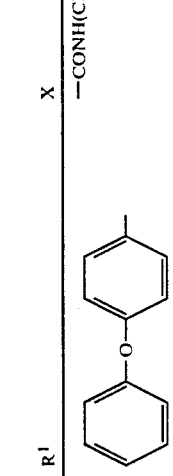 piperidine | —CH₂—phenyl | $C_{27}H_{30}N_3O_2$ | 1.24~2.04(9H, m), 2.76~2.88(2H, bd), 3.3~3.5(6H, slm), 6.1(1H, bt), 6.88~7.74(14H, m) | B |
| 91 | CH₃OCH₂S-phenyl | —CONH(CH₂)₂— | piperidine | —CH₂—phenyl | $C_{23}H_{30}N_3O_2S$ | 1.22~2.06(9H, m), 2.8~2.92(2H, bd), 3.38(3H, s), 3.44(2H, s), 3.28~3.4(2H, m), 4.94(2H, s), 6.36(1H, bt), 7.26(5H, s), 7.4(2H, d), 7.64(2H, d) | B |
| 92 |  CH₃O-phenyl-O- | —CONH(CH₂)₂— | piperidine | —CH₂—phenyl | $C_{27}H_{31}N_3O_2$ | 1.24~2.06(9H, m), 2.88(2H, bd), 3.40(2H, t), 3.40(2H, s), 5.11(2H, s), 5.94(1H, bs), 6.94(2H, d), 7.28(5H, s), 7.32(2H, d), 7.77(2H, d), 8.6(2H, d) | B |
| 93 | 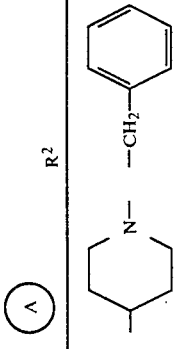 pyridine | —CONH(CH₂)₂— | piperidine | —CH₂—phenyl | $C_{20}H_{21}N_3O$ | 2.9(2H, d), 3.48(2H, s, d), 6.7(1H, bt), 7.28(5H, s), 7.1(1H, ), 7.65(1H, ), 7.9(1H,) | B |
| 94 |  chloropyridine | —CONH(CH₂)₂— | piperidine | —CH₂—phenyl | $C_{20}H_{14}N_3OCl$ | 1.26~2.05(9H, m), 2.8~2.9(2H, bd), 3.32~3.54(4H, slm), 6.56(1H, bt), 7.28(5H, s), 7.34(1H, d), 8.02(1H, dd), 8.7(1H, d) | B |
| 95 | 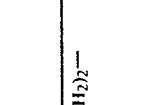 pyrimidine | —CONH(CH₂)₂— | piperidine | —CH₂—phenyl | $C_{27}H_{24}N_4O$ | 1.3~2.07(9H, m), 2.8~2.92(2H, bd), 2.38~2.6(4H, slm), 7.27(5H, s), 7.7(1H, bt), 8.5(1H, s), 8.7(1H, d), 9.38(1H, d) | B |
| 96 |  quinoline | —CONH(CH₂)₂— | piperidine | —CH₂—phenyl | $C_{24}H_{14}N_3O$ | 2.86*2H, d), 3.48(4H, s, d), 6.44(1H, tb), 7.26(5H, s), 7.4~7.8(3H0, 8.4(2H), 8.74(1H, d) | B |

TABLE 2-continued $$R^1-X-\underset{A}{\bigcirc}-R^2$$

| Example | R¹ | X | A | R² | Molecular formula | | Preparation method |
|---|---|---|---|---|---|---|---|
| 97 | 4-pyridyl | —CONH(CH₂)₂— | 4-piperidyl (N—) | —CH₂— phenyl | C₂₀H₁₃N₃O | 2.24~2.56(8H, m), 3.56(2H, s), 4.0(2H, t), 5.28(1H, t), 6.64(1H, bs), 7.31(5H, s), 7.6(2H, dd), 8.66(2H, dd) | B |
| 98 | 4-(4-methylbenzoyl)phenyl | —CON(CH₃)(CH₂)₃— | 4-piperidyl (N—) | —CH₂— phenyl | C₂₇H₃₁N₃O₂·HCl | 0.8~2.10(11H, m), 2.49~2.88 (7H, m), 7.04~7.84(14H, m) | B |
| 99 | 4-(methylsulfonyloxymethyl)phenyl | —CON(CH₃)(CH₂)₃— | 4-piperidyl (N—) | —CH₂— phenyl | C₂₂H₃₀N₄O₃S·HCl | 0.92~2.10(9H, m), 2.44~3.6(7H, m), 3.0(3H, s), 3.44(2H, bd), 7.14 (5H, s), 7.52(2H, d), 7.96(2H, d) | B |
| 100 | 4-pyridyl | —CON(C₂H₅)(CH₂)₃— | 4-piperidyl (N—) | —CH₂— phenyl | C₂₁H₂₁N₃O | 1.02~2.10(12H, m), 2.7~3.7(8H, m), 8.2~8.28*7H, d, s), 8.68(2H, d) | B |
| 101 | 4-pyridyl | —CON(CH₂phenyl)(CH₂)₃— | 4-piperidyl (N—) | —CH₂— phenyl | C₂₇H₂₁N₃O | 1.03~2.04(9H, m), 2.7~3.7(6H, m), 4.44(2H, s), 4.74(2H, s), 7.90~ 7.6(12H, m), 8.64(2H, bs) | B |
| 102 | 4-pyridyl | —CONH(CH₂)₃— | 4-piperidyl (N—) | —CH₂— phenyl | C₂₁H₁₇N₃O | 1.14~2.04(11H, m), 2.78~2.9(2H bd), 3.16~3.76(4H, s, d), 6.5 (1H, s), 7.26(5H, s), 7.56(2H, d), 8.68(2H, d) | B |
| 103 | 4-pyridyl | —CONH(CH₂)₂— | 4-piperidyl (N—) | —CH₂— 4-pyridyl | C₂₇H₂₄N₄O | 1.3~2.1(9H, m), 2.76~2.80(2H, m), 3.16~3.58(4H, m, s), 6.84(1H, s), 7.24(2H, d), 7.6(2H, d), 8.48 (2H, d), 8.68(2H, d) | B |

TABLE 2-continued

R¹—X—(A)—R²

| Example | R¹ | X | (A) | R² | Molecular formula | NMR | Preparation method |
|---|---|---|---|---|---|---|---|
| 104 | pyridyl | —CONH(CH₂)₂— | piperidine | 2,4-dichlorobenzyl (—CH₂—C₆H₃Cl₂) | $C_{20}H_{13}N_3O_2Cl_2$ | 2.0(2H, d), 3.4(4H, s, t), 7.5~7.1(3H), 7.62(2H), 8.64(2H) | B |
| 105 | pyridyl | —CONH(CH₂)₂— | piperidine | 4-pyridylmethyl | $C_{28}H_{12}N_4O$ | 1.22~1.96(7H, m), 2.7~3.0(2H, m), 3.4~3.62(2H, m), 3.8~3.85 (2H, m), 6.62(3H, m, s), 7.58(2H, d), 8.7(2H, d) | B |
| 106 | 4-benzoylphenyl | —CONH(CH₂)₂— | piperidine | 4-pyridylmethyl | $C_{21}H_{17}N_3O_2$ | 1.04~2.16(9H, m), 2.82(2H, d), 3.32~3.62(2H, m), 3.46(2H, s), 6.32~6.58(1H, m), 7.16~8.56 (13H, m) | B |
| 107 | 5-hydroxyphthalimido | —CH₂— | piperidine | benzyl | $C_{21}H_{21}N_3O_4$ | 1.26~2.06(9H, m), 2.78~2.9(2H, bd), 3.45(2H, s), 3.62(2H, d), 7.24(5H, s), 7.95~8.04(1H, m), 8.5~8.6(2H, m) | C |
| 108 | phthalimido | —(CH₂)₂— | piperidine | benzyl | $C_{21}H_{24}N_3O_2$ | 1.26~2.04(9H, m), 2.04(2H, bd), 3.44(2H, s), 3.68(2H, t), 7.24 (5H, s), 7.7(4H, m) | C |
| 109 | 3-aminophthalimido | —(CH₂)₂— | piperidine | benzyl | $C_{21}H_{11}N_3O_2$ | 1.28~2.04(9H, m), 2.85(2H, bd), 3.46(2H, s), 3.62(2H, t), 5.17 (2H, s), 6.78(1H, d), 7.1(1H, d), 7.25(5H, s), 7.36(1H, t) | C |

TABLE 2-continued $$R^1-X-\boxed{A}-R^2$$

| Example | R¹ | X | A | R² | Molecular formula | NMR | Preparation method |
|---|---|---|---|---|---|---|---|
| 110 | (5-amino-isoindolin-2-yl carbonyl, with NH₂) | −(CH₂)₂− | (piperidine, N-linked, 4-position) | −CH₂−phenyl | $C_{21}H_{11}N_3O_2$ | 1.26~2.04(9H, m), 2.84(2H, bd), 3.48(2H, s), 3.6(2H, t), 5.31(2H, s), 6.76(1H, dd), 6.90(1H, d), 7.27(5H, s), 7.54(1H, d) | C |
| 111 | (5-benzamido-phthalimide) | −(CH₂)₂− | (piperidine) | −CH₂−phenyl | $C_{27}H_{17}N_3O_3$ | 1.28~2.05(9H, m), 2.86(2H, bd), 3.50(2H, s), 3.68(2H, t), 7.28(5H, s), 7.50(3H, m), 7.86(3H, m), 8.11(2H, m), 8.36(1H, s) | C |
| 112 | (pyromellitic diimide with CH₂-cyclohexyl-CH₂N linker) | −(CH₂)₂− | (piperidine) | −CH₂−phenyl | $C_{21}H_{11}N_4O_4$ | 2.84(2H, d), 2.44(2H, s), 2.7(2H, t), 7.24(10H, s), 8.2(2H, s) | C |
| 113 | (5-methyl-2-(N-acetylamino)benzamide) | −(CH₂)₂− | (piperidine) | −CH₂−phenyl | $C_{23}H_{17}N_3O_8$ | 1.0~2.2(8H, m), 2.41(3H, s), 2.7~3.1(2H, m), 3.5(2H, s), 4.11(2H, t), 7.8~8.9(8H, m) | D |

TABLE 2-continued

R¹—X—(A)—R²

| Example | R¹ | X | A | R² | Molecular formula | ¹H NMR | Preparation method |
|---|---|---|---|---|---|---|---|
| 114 | 2-(1,3-dioxo-isoindolin-2-yl)phenyl (phthalimide-type structure) | —(CH₂)₂— | piperidine | —CH₂—phenyl | C₂₂H₁₇N₃O₂ | 0.9–2.2(8H, m), 2.7–3.0(2H, m), 3.48(2H, s), 4.06(2H, t), 7.9–8.87(8H, m), 8.0–8.2 (1H, m) | D |
| 115 | ClCH₂S—C₆H₄— | —CONH(CH₂)₂— | piperidine | —CH₂—phenyl | C₂₁H₁₇N₃OSCl·HCl·½H₂O | 0.92–2.04(9H, m), 2.64–3.00(2H, bd), 3.12–3.60(2H, m), 3.40(2H, s), 4.96(2H, s), 6.48–6.76(1H, bt), 7.08–7.84(9H, m) | B |
| 116 | (C₆H₅)₂CH—S(O)—CH₂—C₆H₄— | —CONH(CH₂)₂— | piperidine | —CH₂—phenyl | C₂₂H₃₁N₁O₁S·HCl·½H₂O | 1.0–2.10(9H, m), 2.70–2.96(2H, bd), 3.20–3.60(2H, m), 3.46(2H, s), 4.00(2H, d), 6.20 (1H, bs), 6.84–7.80(14H, m) | B |
| 117 | (C₆H₅)₂CH—CH₂—C₆H₄— | —CONH(CH₂)₂— | piperidine | —CH₂—phenyl | C₂₄H₃₀N₁O·HCl | 1.20(3H, s), 1.28(3H, s), 1.00–2.08(9H, m), 2.64–3.02(3H, m), 3.45(2H, s), 3.24–3.56 (2H, m), 6.36(1H, bt), 7.12–7.76(9H, m) | B |
| 118 | CH₃O—C₆H₄— | —CONH(CH₂)₂— | piperidine | —CH₂—phenyl | C₂₂H₂₆N₃O₂·HCl | 1.00–3.08(14H, m), 2.64–2.96(2H, bd), 3.44(2H, s), 3.32–3.48(2H, m), 3.80(3H, s), 6.76–7.52(9H, m) | B |
| 119 | CH₃CO—C₆H₄— | —CONH(CH₂)₂— | piperidine | —CH₂—phenyl | C₂₂H₂₆N₃O₂·HCl | 1.00–3.08(14H, m), 2.60(3H, s), 3.24–3.62 (2H, bd), 3.46(2H, s), 6.16(1H, bt), 7.26(5H, s), 7.08–8.00(4H, bd) | B |
| 120 | CH₃—C₆H₄— | —CONH(CH₂)₂— | piperidine | —CH₂—phenyl | C₂₁H₁₁N₃O·HCl | 1.03–2.12(14H, m), 2.36(3H, s), 2.68–2.96 (2H, bd), 3.28–3.56(2H, m), 3.44(2H, s), 6.00(1H, bt), 7.08–7.70(9H, m) | B |

TABLE 2-continued

R¹—X—(A)—R²

| Example | R¹ | X | (A) | R² | Molecular formula | NMR | Preparation method |
|---|---|---|---|---|---|---|---|
| 121 |  | —(CH₂)₂— |  | —CH₂—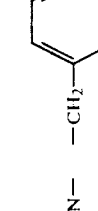 | C₂₂H₁₄N₁O₃.HCl | 1.10~2.08(14H, m), 2.68~2.98(2H, bd), 3.28~3.56(2H, m), 3.46(2H, s), 3.88(3H, s), 3.89(3H, s), 5.94(1H, bt), 6.72~8.44(8H, m) | B |
| 122 |  | —(CH₂)₂— | 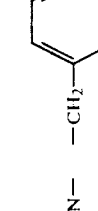 | —CH₂—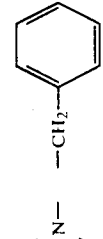 | C₂₁H₂₀N₃O₂.HCl | 0.72~2.48(9H, m), 2.48~3.00(2H, bd), 3.48(2Hs), 3.20~3.60(2H, m), 6.40~6.60(1H, bt), 7.08~7.92(14H, m) | B |
| 123 | 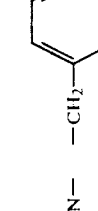 | —(CH₂)₂— | 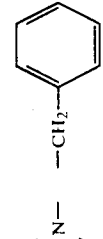 | —CH₂— | C₂₇H₃₄N₁O.HCl | 1.12~3.12(9H, m), 2.68~3.00(2H, bd), 3.45(2H, s), 3.24~3.60(2H, m), 6.24(1H, bt), 7.04~8.20(14H, m) | B |
| 124 | 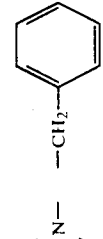 | —(CH₂)₂— |  | —CH₂—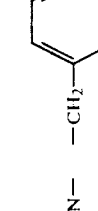 | C₂₁H₃₀N₁O₃.HCl | 0.92~3.08(14H, m), 2.64~2.98(2H, bd), 3.45(2H, s), 3.24~3.60(2H, m), 6.24(1H, bt), 7.04~8.20(14H, m) | B |
| 125 |  | —CONH(CH₂)₂— | 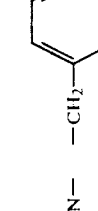 | —CH₂—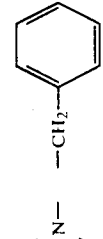 | C₂₁H₁₈N₃O.HCl | 0.96~2.08(14H, m), 2.68~2.96(2H, bd), 3.44(2H, s), 3.28~3.62(2H, m), 3.26(1H, bt), 7.08~8.28(12H, m) | B |
| 126 | 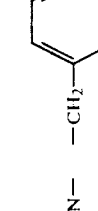 | —CONH(CH₂)₂— | 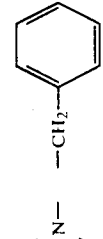 | —CH₂— | C₂₄H₁₁N₃O.HCl | 1.2~2.06(7H, m), 2.80~2.92(2H, bd), 3.33~3.6(2H), 3.46(2H, s), 7.27(5H, s), 7.3~8.54(5H, m) | B |
| 127 | 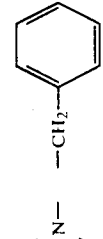 | —CONH(CH₂)₂— |  | —CH₂—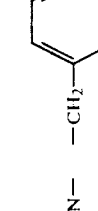 | C₂₁H₁₁N₂OF.HCl | 1.04~2.10(14H, m), 2.68~2.38(2H, bd), 3.46(2H, s), 3.24~3.56(2H, m), 6.06(1H, bt), 6.88~7.84(9H, m) | B |

TABLE 2-continued

| Example | R¹ | X | A | R² | | Molecular formula | H¹-NMR(DCO₃, ppm) | Preparation method |
|---|---|---|---|---|---|---|---|---|
| 128 | CH₂O-C₆H₄- | -CON(CH₃)(CH₂)₃- | N-piperidine | -CH₂- | phenyl | C₂₂H₃₄N₃O₂·HCl | 0.96~3.08(14H, m), 2.60~3.03(2H, bd), 2.97(3H, s), 3.03~3.60(2H, m), 3.45(3H, S0, 3.79(3H, s), 6.72~7.40(9H, m) | B |
| 129 | CH₃O-C₆H₄- | -CON(CH₃)(CH₂)₃- | N-piperidine | -CH₂- | phenyl | C₂₇H₃₄N₃O₂·HCl·½H₂O | 1.04~2.04(9H, m), 2.80(2H, broad d), 2.98 (3H, d)3.20~3.48(2H, m), 3.24(2H, s), 5.06(2H, s), 6.90(2H, d), 7.16~7.44(12H, m) | B |
| 130 | CH₂SO₃-C₆H₄- | -CON(C₂H₅)(CH₂)₃- | N-piperidine | -CH₂- | phenyl | C₃₆H₃₁N₃O₂·HCl·½H₂O | 0.92~1.96(12H, m), 2.60~3.54(8H, m), 4.36(2H, s), 6.96~7.44(12H, m), 7.60(2H, d) | B |
| 131 | pyridyl | -CONHCH₂- | N-piperidine | -CH₂- | phenyl | C₂₈H₁₂N₃O | 1.2~2.08(7H, m), 2.82~2.95(2H, bd), 3.27~3.4(2H, t), 3.48(2H, s), 6.4(1H), 7.26(5H, s), 7.53~7.60(2H), 8.65~8.73(2H) | B |
| 132 | benzoylphenyl | -CONH(CH₂)₂- | N-piperidine | -CH₂- | phenyl | C₂₇H₁₇N₃O₁·2HCl | 1.04~2.20(14H, m), 2.64~2.95(2H, bd), 3.32~3.64(2H, m), 3.46(2H, s), 6.48(1H, bt), 7.12~8.56(13H, m) | B |
| 133 | chlorophthalimidyl | -(CH₂)₂- | N-piperidine | -CH₂- | phenyl | C₂₁H₁₂N₃O₂Cl | 1.07~2.50(9H, m), 2.71~2.82(2H, bd), 3.36(2H, s), 3.5~3.67(2H, t), 7.16(5H, s), 7.46~7.76(3H, m) | C |
| 134 | NO₂-C₆H₄- | -CON(CH₃)(CH₂)₂- | N-piperidine | -CH₂- | phenyl | C₂₂H₂₇N₃O₃ | 1.05~2.04(9H, m), 2.80~3.11(5H, m), 3.50(2H, s), 7.35(5H, s), 7.60(2H, d), 8.30(2H, d), | B |

TABLE 2-continued

R¹—X—(A)—R²

| Example | R¹ | X | A | R² | Molecular formula | | Preparation method |
|---|---|---|---|---|---|---|---|
| 135 | 4-NO₂-C₆H₄- | —CON—(CH₂)₂—<br>   \|<br>   CH₂CH₃ | piperidine (N-) | —CH₂—C₆H₅ | $C_{23}H_{29}N_3O_3$ | 1.05~2.0(9H, m),<br>3.2(2H, d), 3.45(2H, d),<br>7.30(5H, s), 7.50(2H, d), | B |
| 136 | 4-CN-C₆H₄- | —CON—(CH₂)₂—<br>   \|<br>   CH₃ | piperidine (N-) | —CH₂—C₆H₅ | $C_{22}H_{27}N_3O$ | 1.0~2.0(9H, m), 2.65~3.05,<br>(5H, m), 3.45(2H, s),<br>7.30(5H, 2), 7.45(2H, d),<br>7.70(2H, d), 8.30(2H, d). | B |
| 137 | 4-CN-C₆H₄- | —CON—(CH₂)₂—<br>   \|<br>   CH₂CH₃ | piperidine (N-) | —CH₂—C₆H₅ | $C_{23}H_{29}N_3O$ | 1.0~2.0(9H, m), 2.8(2H, d),<br>3.14(2H, s), 3.45(2H, s),<br>7.30(5H, s), 7.35(2H, d),<br>7.60(2H, d). | B |

In order to show the effects of the compounds of the invention in detail, part of examples of pharmacological experiments using animals will be described hereinunder.

In addition to the working examples disclosed above in view of the pharmacological tests, the compound of the invention was examined in view of effects on scopolamine-induced impairment of passive avoidance, using ddY male mice. As a result it was found that it had an excellent activity in this respect.

EXPERIMENTAL EXAMPLE 1

Acetylcholinesterase Inhibitory Action using Mouse Brain Homogenate

Using a mouse brain homogenate as a source of acetylcholinesterase, the esterase activity was measured by a thiocholine method. Acetylcholine as a substrate, the compound of the invention as a substance to test and 5,5'-dithio-bis(2-nitrobenzoic acid), called also DTNB, were added to the mouse brain homogenate. After incubation, thiocholine produced was reacted with DTNB to form a yellow product. The acetylcholinesterase activity was determined by the measurement of the absorbance change of the reaction product at 412 nm.

The acetylcholinesterase inhibitory activity of the compound tested was expressed in terms of the 50% inhibitory concentration, IC50.

Results are shown in Table 3.

TABLE 3

| Compound (Example No.) | AchE inhibitory activity IC$_{50}$ ($\mu$M) | Compound (Example No.) | AchE inhibitory activity IC$_{50}$ ($\mu$M) |
| --- | --- | --- | --- |
| 4 | 0.0006 | 56 | 0.0033 |
| 5 | 0.088 | 57 | 0.0012 |
| 6 | 0.021 | 58 | 0.013 |
| 7 | 0.014 | 62 | 0.0034 |
| 8 | 0.08 | 68 | 0.0045 |
| 9 | 0.0055 | 71 | 0.055 |
| 10 | 0.0042 | 88 | 0.049 |
| 16 | 0.059 | 98 | 0.0083 |
| 21 | 0.021 | 110 | 0.0088 |
| 25 | 0.0045 | 111 | 0.00088 |
| 26 | 0.009 | 112 | 0.00015 |
| 32 | 0.0043 | 113 | 0.0047 |
| 41 | 0.0008 | 115 | 0.0067 |
| 47 | 0.009 | 116 | 0.009 |
| 48 | 0.0039 | 122 | 0.02 |
| 50 | 0.0028 | 123 | 0.0105 |
| 51 | 0.0022 | 130 | 0.0003 |
| 52 | 0.0015 | 133 | 0.0079 |
| 53 | 0.0024 | Physo *1 | 0.89 |
| 54 | 0.008 | THA *2 | 0.084 |

(Notes)
*1; physostigmine
*2; 1, 2, 3, 4-Tetrahydro-9-Aminoacridine

EXPERIMENTAL EXAMPLE 2

Acute Toxicity Test for ddY Male Mouse

Acute toxicity test was carried out using ddY male mice.

The results are shown in Table 4

TABLE 4

| Compound (Example No.) | Oral to mouse (mg/kg) 100 mg | Oral to mouse (mg/kg) 300 mg |
| --- | --- | --- |
| 4 | 0/3 *1 | 2/4 *1 |
| 5 | ⅓ | 4/4 |
| 7 | — | 0/3 |
| 10 | ⅔ | — |

(Notes)
*1; Denominator shows the number of Animals used, and numerator shows the number of deaths.

What is claimed is:

1. A piperidine derivative having the formula (I) or a pharmacologically acceptable salt thereof:

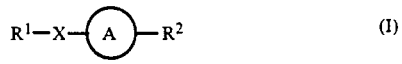

wherein
R$^1$ is

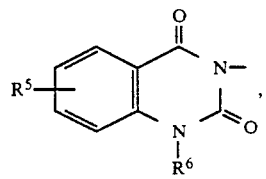

R$^5$ being hydrogen, methyl or chlorine and R$^6$ being hydrogen, methyl or chlorine, X is

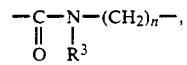

wherein n is an integer of 1 through 7 and R$^3$ is hydrogen, lower alkyl or benzyl,

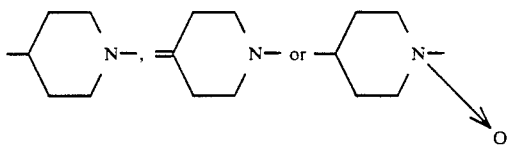

and R$^2$ is hydrogen, lower alkyl, benzyl, benzyl substituted by hydroxy, methoxy or chlorine, benzoyl, benzoyl with a fluorine substituent, pyridyl, 2-hydroxyethyl, pyridymethyl or a group of the formula

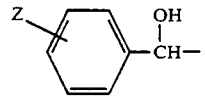

wherein Z represents a halogen atom.

2. A piperidine derivative or a pharmacologically acceptable salt thereof as claimed in claim 1, in which the ring A is

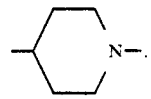

3. A piperidine derivative or a pharmacologically acceptable salt thereof as claimed in claim 1, in which X is

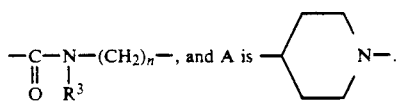, and A is 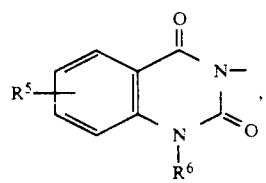

4. A piperidine derivative or a pharmacologically acceptable salt thereof as claimed in claim 3, in which $R^2$ is benzyl or benzyl substituted with hydroxy, methoxy or chlorine.

5. A piperidine derivative or a pharmacologically acceptable salt thereof as claimed in claim 1, in which n is 2.

6. A pharmaceutical composition which comprises the piperidine derivative as defined in claim 1 and a pharmacologically acceptable carrier.

7. A method for treating dementias and sequelae of cerebrovascular diseases which comprises administering to a patient requiring such treatment a pharmacologically effective amount of the piperidine derivative as defined in claim 1.

8. A piperidine derivative having the formula (I) or a pharmacologically acceptable salt thereof:

$$R^1-X-\underset{A}{\bigcirc}-R^2 \quad (I)$$

wherein
$R^1$ is

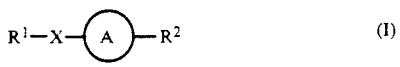, $R^5$ being hydrogen, methyl or chlorine and $R^6$ being hydrogen, methyl or chlorine,
X is —O(CH$_2$)$_n$—, —S(CH$_2$)$_n$—, —NH(CH$_2$)$_n$—, —SO$_2$NH(CH$_2$)$_n$—, —NH—C—(CH$_2$)$_n$—, —NH(CH$_2$)$_n$—C—, —C—O(CH$_2$)$_n$—,
     ‖                        ‖        ‖
     O                        O        O —CH$_2$NH(CH$_2$)$_n$—, —C—N—(CH$_2$)$_n$—,
                      ‖  |
                      O  R$^3$ wherein n is an integer of 1 through 7 and $R^3$ is hydrogen, lower alkyl or benzyl,

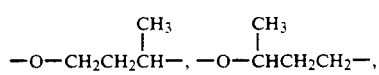

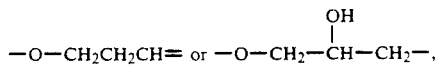

A is

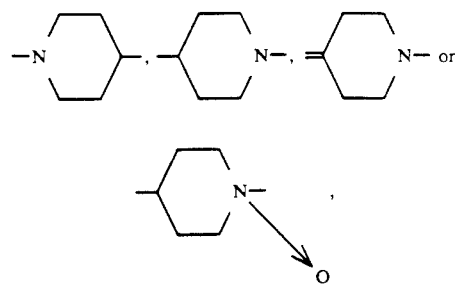

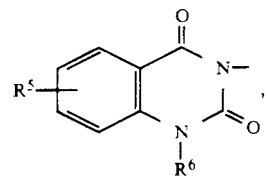

and $R^2$ is hydrogen, lower alkyl, benzyl, benzyl substituted by hydroxy, methoxy or chlorine, benzoyl, benzoyl with a fluorine substituent, pyridyl, 2-hydroxyethyl, pyridylmethyl or a group of the formula

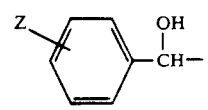

wherein Z represents a halogen atom.

9. A piperidine derivative having the formula (I) or a pharmacologically acceptable salt thereof:

$$R^1-X-\underset{A}{\bigcirc}-R^2 \quad (I)$$

wherein
$R^1$ is

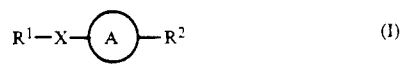, $R^5$ being hydrogen, methyl or chlorine and $R^6$ being hydrogen, methyl or chlorine,
X is —O(CH$_2$)$_n$—, —S(CH$_2$)$_n$—, —NH(CH$_2$)$_n$—, —SO$_2$NH(CH$_2$)$_n$—, —NH—C—(CH$_2$)$_n$—, —NH(CH$_2$)$_n$—C—, —C—O(CH$_2$)$_n$—,
     ‖                        ‖        ‖
     O                        O        O —CH$_2$NH(CH$_2$)$_n$—, wherein n is an integer of 1 through 7 and $R^3$ is hydrogen, lower alkyl or benzyl,

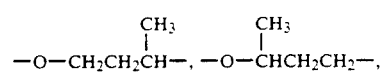

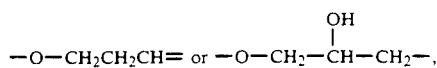

A is

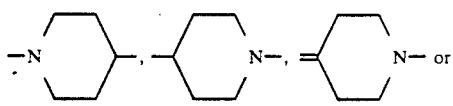
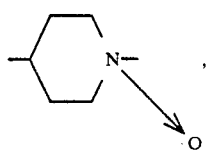
and R² is hydrogen, lower alkyl, benzyl, benzyl substituted by hydroxy, methoxy or chlorine, benzoyl, benzoyl with a fluorine substituent, pyridyl, 2-hydroxyethyl, pyridylmethyl or a group of the formula
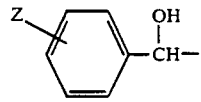
wherein Z represents a halogen atom.
* * * * *

UNITED STATES PATENT AND TRADEMARK OFFICE
CERTIFICATE OF CORRECTION

PATENT NO. : 5 306 720

DATED : April 26, 1994

INVENTOR(S) : Hachiro SUGIMOTO et al

It is certified that error appears in the above-identified patent and that said Letters Patent is hereby corrected as shown below:

```
Column 66, line 37; after "benzyl," insert
            ---A is---.
```

Signed and Sealed this

Eleventh Day of October, 1994

Attest:

BRUCE LEHMAN

Attesting Officer     Commissioner of Patents and Trademarks